United States Patent [19]
Sakka et al.

[11] Patent Number: 5,271,902
[45] Date of Patent: Dec. 21, 1993

[54] QUANTITATIVE LIQUID SAMPLING INSTRUMENT

[75] Inventors: Toshiaki Sakka; Yukio Mitsuhisa, both of Yokohama, Japan

[73] Assignee: Tosoh Corporation, Shinnanyo, Japan

[21] Appl. No.: 800,412

[22] Filed: Dec. 2, 1991

[30] Foreign Application Priority Data

Nov. 30, 1990 [JP] Japan .................... 2-333804

[51] Int. Cl.$^5$ ............................... B01L 3/02
[52] U.S. Cl. ...................... 422/100; 422/58; 422/106; 422/107; 436/54; 73/863.01; 250/577
[58] Field of Search ............... 422/100, 58, 106, 107; 436/180, 54; 73/863.01, 864.23–864.25; 250/577

[56] References Cited

U.S. PATENT DOCUMENTS

| | | | |
|---|---|---|---|
| 2,912,858 | 11/1959 | Fuller | 250/577 |
| 3,314,292 | 4/1967 | Schulte et al. | 250/577 |
| 3,683,196 | 8/1972 | Obenhaus | 250/577 |
| 4,053,002 | 10/1977 | Ludlow | 141/95 |
| 4,410,020 | 10/1983 | Lorenz | 422/55 |
| 4,846,003 | 7/1989 | Marquiss | 73/864.24 |
| 4,944,922 | 7/1990 | Hayashi | 422/100 |
| 5,045,286 | 9/1991 | Kitajima et al. | 422/100 |

FOREIGN PATENT DOCUMENTS

| | | |
|---|---|---|
| 0038912 | 11/1981 | European Pat. Off. |
| 0250671 | 1/1988 | European Pat. Off. |
| 2627861 | 9/1989 | France |
| WO87/07946 | 12/1987 | PCT Int'l Appl. |

Primary Examiner—Robert J. Warden
Assistant Examiner—Hien Tran
Attorney, Agent, or Firm—Oblon, Spivak, McClelland, Maier & Neustadt

[57] ABSTRACT

A quantitative liquid sampling instrument comprises a main body of a pipet device which includes a pipet tip having an opening at its lower end for sucking and discharging a liquid. The pipet tip being in a shape of a tube shell having a cavity for holding a liquid sucked therein through the opening and being made of a transparent or semi-transparent material. The main body further comprising a device for applying a gas pressure for sucking or discharging the liquid to or from the inside of the cavity of the pipet tip. The instrument further comprising a liquid level detecting device installed under the main body of the pipet device; a vertical movement control device for moving the main body of the pipet device or a container of the liquid to make them relatively approach one another until a predetermined length of the lower end of the pipet tip is dipped into the liquid in the container; and a computing device for computing the end point of relative approaching movement of the main body of the pipet device and the container and for outputting a signal regarding the end point to the vertical movement control device.

9 Claims, 5 Drawing Sheets

QUANTITATIVE LIQUID SAMPLING INSTRUMENT

BACKGROUND OF THE INVENTION

1. Field of the Invention

The present invention relates to a quantitative liquid sampling instrument for taking out an extremely small quantity of a liquid sample, a liquid reagent or the like quantitatively.

2. Description of the Related Art

In the microanalysis of biological samples, or the like, it is necessary to take out an extremely small amount of a sample or a reagent quantitatively from a container with high accuracy, and to dispense the taken sample into a reaction vessel or the like. Specially constituted systems and apparatuses are used therefor.

Usually in analysis and measurement employing such systems, only a small amount of a sample is available, or an extremely minor component like an antibody or protein in blood is determined, and furthermore, variations in quantity of the sample taken out will induce critical errors in the measurement result. Accordingly micropipets are generally used which enable the taking out of a micro-quantity of samples with high accuracy. Further, since contamination in the sample will interrupt the achievement of correct analysis data, automated apparatuses are desired for treating a number of samples successively. For the purpose of taking out and dispensing successively a number of samples, many systems are developed in which tips of the disposable type are used for the pipets of the micropipet instrument, or a tip washing step is incorporated in the system.

The micropipet instruments are operated in such a manner that the tip (or the lower end) of the pipet is inserted into a sample container, and a predetermined quantity of a liquid sample is sucked into the pipet by a negative air pressure, and subsequently the taken sample is dispensed into a reaction vessel or the like by a positive air pressure. In this operation, the pipet tip is washed, or is preferably replaced by a new one for every sample.

In the aforementioned micropipet type of quantitative liquid sampling instrument, special consideration should be given to the control of the position of the pipet tip relative to the level of the liquid sample in order to take out a liquid sample with high accuracy.

In immune reaction measurement, biochemical analysis, or the like, sample containers have generally a small opening having a diameter of as small as 15 mm or less, so that quantitative sampling of relatively viscous liquid samples like blood are greatly affected by the meniscus of the liquid. Unless the level of the liquid to be brought into contact with the pipet tip is precisely detected, the inconvenience arises that an excessively large amount of the sample may be introduced into the pipet, or a required amount of the liquid cannot be taken out precisely. When an excessive amount of the liquid sample is introduced to the pipet, the liquid sample attached to the wall of the pipet may run down during dispensation of the sample, causing disadvantageous variation in the amount dispensed. Frequently in immune reaction measurement, samples are taken out from one sample container repeatedly to utilize the whole sample effectively. In such a case, the pipet may inconveniently strike against the bottom of the sample container at the final quantitative sampling from the same container. Accordingly, the depth of dipping of the pipet needs to be detected precisely.

Provided that an "invariable quantity" of samples such as biological samples are always contained in an "invariable shape" of sample containers, it is generally understood that mere control of the descending of the pipet to a fixed position enables accurate quantitative sampling with high accuracy.

Practically, however, the quantities of a liquid sample in sample containers are rarely constant and the level of the liquid usually varies in every container, even if the container has a uniform diameter (namely having a constant horizontal sectional area). Therefore, in order to insert the pipet to a predetermined depth precisely into the liquid for quantitative sampling, it is very important in such types of quantitative liquid sampling instruments to detect the liquid level in the container for every sample and to decide the pipet inserting depth depending on the detected information.

In the fields of biochemistry and analytical chemistry, as discussed above, especially in immune reaction measurement, liquid level height (position) in a container needs to be measured for sampling quantitatively a microquantity of liquid samples, and in particular, a mechanical or automated quantitative liquid sampling instrument requires indispensably a liquid level detection device.

In the fields to which the present invention is directed, since liquid level detection technique is necessary, many specific instruments have been proposed, and developed for practical use in view of the prevention of contamination.

The liquid level detecting devices of conventional quantitative liquid sampling instruments, however, are not suitable for repeated measurements of liquid levels since the steps of liquid level detection and liquid suction are separately conducted, resulting in lower operation efficiency disadvantageously.

One example of a conventional quantitative liquid sampling instrument for biological samples in the types as mentioned above employs a non-contact type of optical liquid level detecting device which utilizes an optical reflection type of sensor, in which the distance to the liquid level is detected by bringing the sensor close to the liquid surface with downward light projection and the distance to the liquid surface is detected from the change in the measured intensity of the reflected light. This system, however, involves difficulty in achieving consistently stable measurement of various kinds of samples because the reflection from the liquid surface depends on the shape and inclination of the liquid surface, and further involves difficulty in conducting accurate measurement owing to ambiguity in detection of abrupt change of intensity of the reflected light as the liquid level detection information.

In the case where the sample in the container to be taken out is in an extremely small quantity, the diameter of the opening of the container for sucking with a pipet is small, since a large diameter of the container gives insufficient depth of the small quantity of the liquid, which causes a pipet tip to strike against the bottom of the container, preventing suction of the liquid sample. With such a small diameter of the container, it is not easy to bring the pipet and the sensor, etc. of a liquid detection device simultaneously close to the liquid face in the container, which results in a disadvantage in operation in that the liquid sucking step is necessarily separated from the liquid level detecting step.

On the other hand, liquid level detecting devices of contact type are also known which employ an electrode as the sensor, and detects the liquid level by an abrupt change of the electric current in the electrode upon contact with the liquid. Although this type of device advantageously gives a higher detection sensitivity in comparison with the non-contact type ones, the devices necessarily cause contamination by contact of the electrode with the liquid, even if a disposable type of pipet tip is employed as the pipet for the device. Therefore, such contact type devices are not suitable for microanalysis such as immune reaction measurement. Naturally, the disadvantage of contamination can be avoided by exchanging the electrode for every sample. Such a device, however, is not practical. Further, in the contact type of liquid level detecting device, the contact position of the pipet with the liquid usually deviates from the position of liquid level detection in the horizontal direction, whereby the shape or the inclination of the meniscus of the liquid sample gives much more remarkable influence in comparison with the above-mentioned non-contact optical liquid level detecting device.

For uses other than those to which the present invention is directed, another contact type of liquid level contacting device is known which utilizes the phenomenon that a ray of light introduced into a transparent body at an angle larger than the critical angle and reflected totally will be emitted outside when the transparent body is brought into contact with a different external substance. (See, for example, Japanese Patent Application Laid-Open Nos. Sho 53-55191, Sho 53-91779, and Sho 60-22730).

This type of liquid level detecting device is capable of detection at higher sensitivity in comparison with the non-contact reflection type of device using light similarly. However, in using this type of device for sampling a micro-quantity of a liquid sample, the transparent body for liquid level detection is inserted together with the pipet simultaneously into the sample container of a small diameter. This simultaneous insertion is difficult, so that the liquid level detection and the liquid suction have to be conducted disadvantageously in separate and successive steps. Further, this type of device involves the problem of horizontal deviation of the liquid level detection point from the liquid sucking pipet position, and the problem of contamination by the previous samples is encountered similarly as that in the above electrode type liquid level detection device because of the contact type of detection.

SUMMARY OF THE INVENTION

Accordingly, an object of the present invention is to provide for a novel quantitative liquid sampling instrument which can conduct precise liquid sampling by detecting the liquid level of the sample without the problems involved in the related art.

A further object of the present invention is to provide for a novel quantitative liquid sampling instrument which can simultaneously and rapidly conduct liquid level detection and liquid sample suction of a micro-quantity liquid sampling instrument.

A still further object of the present invention is to provide for a novel quantitative liquid sampling instrument which is free from the contamination between samples by simply employing a disposable type of pipet tip.

The present invention provides a quantitative liquid sampling instrument comprising: (1) a main body of a pipet device comprising a pipet tip having an opening at its lower end for sucking and discharging a liquid, the pipet tip being in a shape of a tube shell having a cavity for holding a liquid sucked therein through the opening and being made of a transparent semi-transparent material; a pipet tip fitting portion to which a pipet tip is detachably fitted; and means for applying a gas pressure for sucking or discharging the liquid to or from the inside of the cavity of the pipet tip fitted to the pipet fitting portion; (2) liquid level detecting means installed under the main body of the pipet device; (3) vertical movement control means for moving the main body of the pipet device or a container of the liquid to make them approach relatively until a predetermined length of the lower end of the pipet tip is dipped into the liquid in the container; and (4) computing means for computing the end point of relative approaching movement of the main body of the pipet device and the container and for outputting a signal regarding the end point to the vertical movement control means; the above-mentioned liquid level detecting means comprising light projecting means for projecting light to the lower end face of the pipet tip and light receiving means for receiving the light reflected by the lower end of the pipet tip, and employing the intensity of the received light as the detection information.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1(a) and FIG. 1(b) schematically illustrate the constitution of the quantitative liquid sampling instrument of Example 1. FIG. 1(a) illustrates the tip not contacting with the liquid. FIG. 1(b) illustrates the tip contacting with the liquid;

DESCRIPTION OF THE PREFERRED EMBODIMENT

The instrument which realizes the intended objects of the present invention has been provided on the basis of the experience below.

In consideration of the combined operation of quantitative sampling and liquid level detection, the pipet is indispensably brought into contact with the liquid in the liquid sampling operation. The contact of a body with a liquid is conducted also in the liquid level detection with an electrode and in the detection with a contact type optical liquid level detecting device in different application fields.

Having noticed this fact, the inventors of the present invention intended to utilize a pipet simultaneously for a constituting member of a liquid level detecting device, although the pipet is a tool for sucking a liquid and is normally not for liquid level detection.

As the results, the inventors have succeeded in using the liquid-sampling pipet simultaneously as a constituting member of a liquid level detecting device. Consequently, the following facts were confirmed: the numbers of the constituting members of the devices are reduced; a liquid level can be detected in high accuracy and further, quantitative sampling of a liquid in high accuracy are made feasible; the operations of liquid level detection and quantitative liquid sampling are unified to result in quickening of the operations; the contamination between samples is readily prevented by use of a pipet of a disposable type; and the unified constitution of the device is highly useful for quantitative sampling of a micro-quantity of liquid such as a biological sample.

The instrument of the present invention may be simplified by unifying the pipet tip with the main pipet instrument in one body and combining a washing means for washing the liquid-contacting portion of the pipet tip. Such a simplified instrument of the present invention requires less work for washing operations with less liability of contamination because the liquid-contacting member is limited only to the sampling pipet which serves also as a contact type of liquid level detecting device.

In the instrument of the present invention, the shape of the pipet tip of the pipet device is not limited provided that its lower end is capable of being inserted into a small container (such as a cup-shaped container and a test tube) and is capable of sucking a liquid into the pipet. Generally those in a shape approximately of an inverted truncated cone are preferably used. The shape of the lower end face of the pipet tip is not specially limited but is preferably designed such that the face functions as a total reflection surface for a downward light beam from the top in a non-liquid-contacting state, typically being formed as a horizontal plain end face. The lower end face of the pipet tip in the present invention naturally includes the end faces visible to naked eyes, but is not limited thereto. For example, a pipet tip, which is made of a thermoplastic material and is stretched with heating into a sharp needle shape, has no distinct end face to the naked eyes. Such a pipet tip is shown experimentally to be useful for the liquid level detection by use of reflected light from the pipet lower end face of the present invention. Accordingly, the above-mentioned "lower end face" denotes collectively the interface between the lower end portion of the pipet tip and the surrounding space.

The material for the pipet tip includes materials which are transparent as well as semi-transparent excluding opaque bodies which intercept light. Particularly preferred materials specifically include polypropylene, polystyrene, acrylics polymethacrylates, polyethylene, and poly-4-methyl-1-pentene. An example of a tip made of such a material is a CRYSTAL LONG TIP (1 to 200 $\mu$l) made by Wakenyaku K. K. Other examples of disposable type of tips are those made of a commercial polypropylene such as STANDARTIPS (1 to 100 $\mu$l) made by Eppendorf Co.

With a pipet instrument having a pipet tip of such a shape and material, light projected toward the lower end face of the pipet tip is strongly reflected (e.g., reflected totally) at the lower end face to be detected by a light-receiving means as large reflection intensity. When this pipet tip is brought into contact with a liquid, the interfacial condition changes to decrease the difference of the refractive indexes, thereby abruptly decreasing the reflective light intensity. As a typical example in which the refractive index of the material of the pipet tip is nearly equal to that of the liquid, almost all of the light totally reflected in the non-liquid contacting state comes to be introduced into the liquid on contact with the liquid, whereby the intensity of the reflected light abruptly drops from a certain level. The instrument of the present invention is constituted by applying this principle to the pipet of the instrument for quantitative sampling of micro-quantity of liquid.

In practical operations of the quantitative liquid sampling instrument of the present invention, a diluting liquid may be preliminarily (or later) sucked into the pipet without any inconvenience in operation of the instrument since the diluting liquid is normally light-transmissive. Further, as described later, an instrument which is not affected by existence of a liquid in the pipet tip can be constituted by establishing a selective light path for light projection and light receiving. In the case where a transparent dilution liquid is sucked firstly into the pipet and liquid sample is sucked subsequently therein, the intensity of the received light is larger advantageously owing to the light reflected by the lower interface of the diluting liquid. Otherwise with a light source provided inside a pipet tip, the light efficiency of the light source is advantageously higher because the light from the light source is readily introduced by the upper interface of the diluting liquid into the tip material.

The instrument of the present invention is particularly effective in taking out quantitatively a sample in an extremely small amount of from 1 to 1000 $\mu$l, particularly from 1 to 150 $\mu$l, but is not limited by the handling volume of samples in principle. In many cases, apparatuses for treating an extremely small amount of liquid like an apparatus for immune measurement handle a number of sample containers holding about 200 $\mu$l of a sample and about 1 cm in diameter. In such cases, it is practically not feasible to bring a pipet together with a separate liquid-level detecting member simultaneously close to the liquid face in the container. However, the above constitution of the present invention enables detection of the liquid level and suction of the liquid practically in one step, since only a pipet tip which serves both to suck the liquid and to detect the liquid face has to be brought close to or contact with the liquid face in a container having a small inside diameter.

The instrument of the present invention having the above-mentioned arrangement includes various embodiments in practical uses. For example, the container may be moved vertically to bring the pipet tip into contact with the sample in the container without any inconvenience, although a pipet vertical-driving mechanism is generally employed.

The path of the light projected to or reflected by the pipet tip end face for liquid level detection may be either in the inside of the tube shell of the pipet tip or in the outside thereof. Particularly preferred is the type utilizing the pipet tip tube shell as the light transmitting medium. In the case where the pipet tube shell which is made of a highly light-transmissive material is utilized as the light transmitting material to transmit the projected light or reflected light, the influence such as diffusion of light is reduced, enabling decrease of light intensity of the light source. Further in that case, the mechanical constitution may be made spatially roomy by arranging the received light sensor in opposition to the upper end face of the pipet tip as the light transmitting medium.

Further, in addition to the use of the pipet tip as the light-transmitting medium, particularly a preferred arrangement includes a light-transmitting medium having a columnar portion and an annular portion opposed to the annular upper end face of the pipet tip, and a received-light sensor provided at the upper end face of the columnar light-transmitting medium. With such a constitution, the reflected light from the lower end face of the pipet tip is effectively utilized as the light for received-light sensor, thereby the abrupt change of the reflected light intensity being detectable more precisely, or the intensity of the light source being reduced.

For the light source of the light projecting means and the received light sensor mentioned above, a light emitting element such as various LED and semiconductor laser, and photodiode and the like are appropriately employed without limitation. The projection of light may be continuous or in pulse. The use of optical fiber for projection and reception of light is often preferred for securing freeness of mechanical design of the instrument.

The light for liquid level detection is not limited, but is preferably the light in the region of ultraviolet light of from 200 to 1100 nm, visible light, and infrared light, particularly preferably in infrared region. In a bright place like a bright room where the usual operation of the instrument is conducted, the received light sensor may react to room illumination or other light. Therefore the wavelength of light is selected as above to stabilize the operation of the apparatus and to improve the accuracy without external light disturbance. If a sample to be sucked into the pipet tip is turbid, a longer wavelength of light is generally advantageous since it causes less light scattering. The selection of the wavelength can be made by selection of the light source and the received light sensor, or by use of an appropriate light filter.

The computing means for detecting the pipet liquid contact from the detection information of abrupt change (or abrupt fall) of the reflected light intensity is generally constituted from a microprocessor, but is not limited thereto. The time of the abrupt change is judged from various phenomena such as a fall of the reflected light intensity below a predetermined threshold value, and a rise of the decreasing rate of the reflected light intensity above a predetermined rate.

The end point of the downward movement of the pipet can be designed so as to be sufficient for taking out the sample.

Specifically the quantitative liquid sampling instrument of the present invention is particularly useful, for example, for immune diagnosis apparatuses which conduct diagnosis by determining quantitatively a minute quantity of protein or the like in blood by immune reaction, and biochemical reaction apparatuses and analysis apparatuses which require quantitative sampling of an extremely small amount of liquid.

The instrument of the present invention, in which a pipet tip only is brought into contact with a liquid, enables simultaneous operations of a contact type liquid level detection and of liquid sucking with high accuracy.

The present invention is described in reference to examples shown in the drawings.

EXAMPLE 1

Figure 1A:
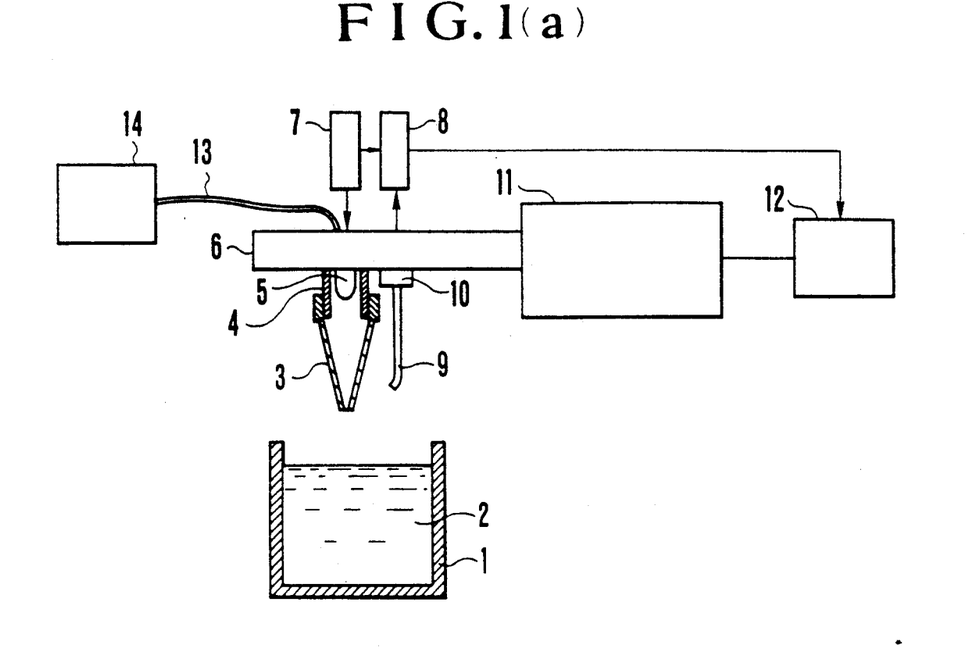
Figure 1B:
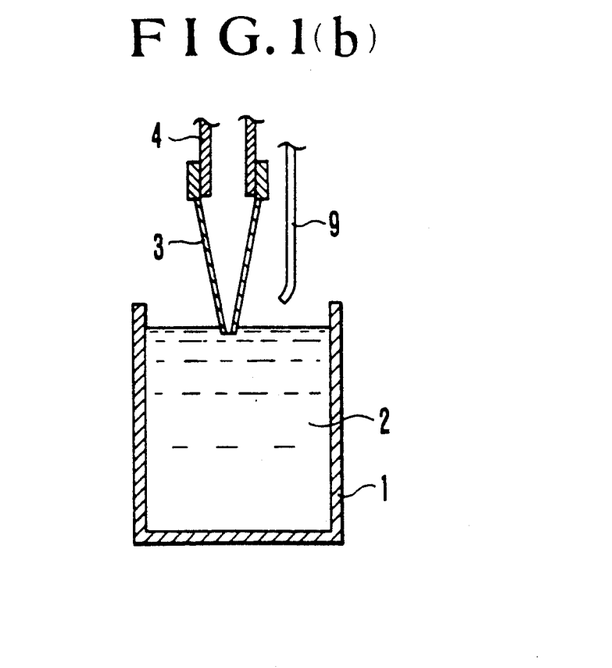

FIG. 1 illustrates an outline of the arrangement of the quantitative liquid sampling instrument of the present invention employing a disposable type of pipet tip used, for example, for immune reaction measurement. FIG. 1(a) shows the state of the instrument before the pipet tip is inserted into a sample solution (namely a solution to be detected). FIG. 1(b) shows the state that the lower end of the pipet tip is inserted into the liquid sample and is sucking the liquid sample.

In the drawings, the sample container 1 contains liquid sample 2 such as a small amount of blood, for example, about several $\mu$l. The liquid sample 2 is introduced into the quantitative liquid sampling instrument which is incorporated in an immune reaction measurement apparatus not shown in the drawing.

A pipet tip fitting tube portion 4 and a frame 6 integrated therewith make-up the main body of the pipet instrument.

A disposable type pipet tip 3 is fitted detachably to the pipet tip fitting tube portion 4 of the main body of the instrument, and is attached to and detached from the pipet tip fitting tube portion 4 at a predetermined waiting position by an attaching-detaching device not shown in the drawing. The pipet tip 3 is made of a light transmissive material as described above.

A light source 5 is fixed to the frame 6 at the inside of the pipet tip fitting tube portion 4 such that a ray of light of a predetermined wavelength is emitted downward from a light-emitting diode inside the pipet tip. The light source 5 is connected electrically to a lighting circuit 7 so as to conduct pulse-lighting.

A vertical movement mechanism 11 moves the frame 6 of the main body of the pipet instrument from an upper waiting position (see FIG. 1(a)) downward to a lower movement end point (see FIG. 1(b)) by a pulse-motor type mechanism (or a turning screw type, or cylinder type), and then returns it to the waiting position, by control of a driving control device 12.

An optical fiber 9 is a portion of a light receiving means hanging down from the frame 6. The light-receiving end face at the lower end of the optical fiber 9 is opposed to the pipet tip 3 at the obliquely upper position so as to take out the reflected light at the lower end face of the pipet tip 3. The upper end of the optical fiber 9 is connected to a photodiode 10 installed on the frame 6. The photodiode 10 generates an electromotive force in accordance with the intensity of the received light. A detection circuit 8 detects the signal derived from the electromotive force, outputs a signal to the driving control device 12. In this example, a light-emitting element as the light source 5 is made to emit light in pulse which is synchronized with the detection timing of the above detection circuit 8 to cancel the influence of external disturbance such as room illumination and the like.

A volume controller 14, such as an air cylinder, is connected to the cavity in the pipet tip 3 through a tube 13 to generate a negative pressure for sucking liquid and a positive pressure for discharging the liquid. The stroke length of the piston in the air cylinder is adjustable.

The operation of the above-mentioned quantitative liquid sampling instrument is described below.

First, the instrument waits at the state shown in FIG. 1(a). In this state, pipet tip 3 is attached to the pipet tip fitting tube portion by a pipet tip attaching-detaching device not shown in the drawing. The instrument is waiting in this state at the upper waiting position (see FIG. 1(a)). Thereto a predetermined sample container 1 is introduced and placed at the lower position for taking the liquid by means of a suitable conveyer or the like.

Subsequently, the frame 6 starts its downward movement with the aid of the vertical movement mechanism 11, and the light-emitting source 5 starts pulse-lighting. A portion of the light emitted downward from the light-emitting source 5 is transmitted through the inside of the pipet tip 3 and is reflected by the lower end face. The reflected light is transmitted through the optical fiber 9 which is placed in an obliquely upper position in opposition to the lower end of the pipet tip 3, and is received by the photodiode 10, causing detection of constant intensity of light in the detection circuit 8.

As the pipet moves downward, the light reflected by the liquid surface comes to be introduced to the photodiode 10, thus increasing gradually the received light intensity in the detection circuit 8.

When the lower end of the pipet tip 3 is brought into contact with the liquid sample as the result of further downward movement, the reflection condition abruptly changes because of the decrease of the refractive index difference at the interface caused by the change from the refractive index of air with which the lower end of the pipet tip was surrounded to the refractive index of the liquid sample brought into contact. Therefore, the reflection at the lower end face of the pipet tip is practically canceled, resulting in the reflected light intensity of nearly zero at the photodiode 10.

Therefore the contact of the pipet tip 3 with the liquid can be readily detected by the abrupt decrease of the reflected light intensity.

The pipet device brought into contact with the liquid is further moved downward and stopped at a predetermined depth of the tip. At this position, the liquid is sucked by driving the air cylinder (volume controller 14). The liquid suction is stopped by the stopping of the cylinder drive.

With the above arrangement, the liquid sample can be sucked into the pipet accurately by the air cylinder stroke at the position where the downward movement of the pipet tip has been stopped.

The predetermined distance of the downward movement of the pipet after the contact with the liquid is decided also in consideration of avoiding the contamination of the subsequent sample caused by contact of the optical fiber 9 of the light-receiving means with the liquid sample. This distance of the downward movement cannot be determined independently of the amount of the sample, the diameter of the container, the amount of the liquid to be taken out, and so forth. In immune reaction measurement apparatuses, for example, the distance is about several mm in many cases for the purpose of obtaining a high accuracy of detection. When a relatively large dipping distance from the contact point is required, such a constitution may be adopted in which the downward movement of the optical fiber 9 is stopped on contact with the liquid and the pipet tip 3 only is moved downward.

Figure 2:
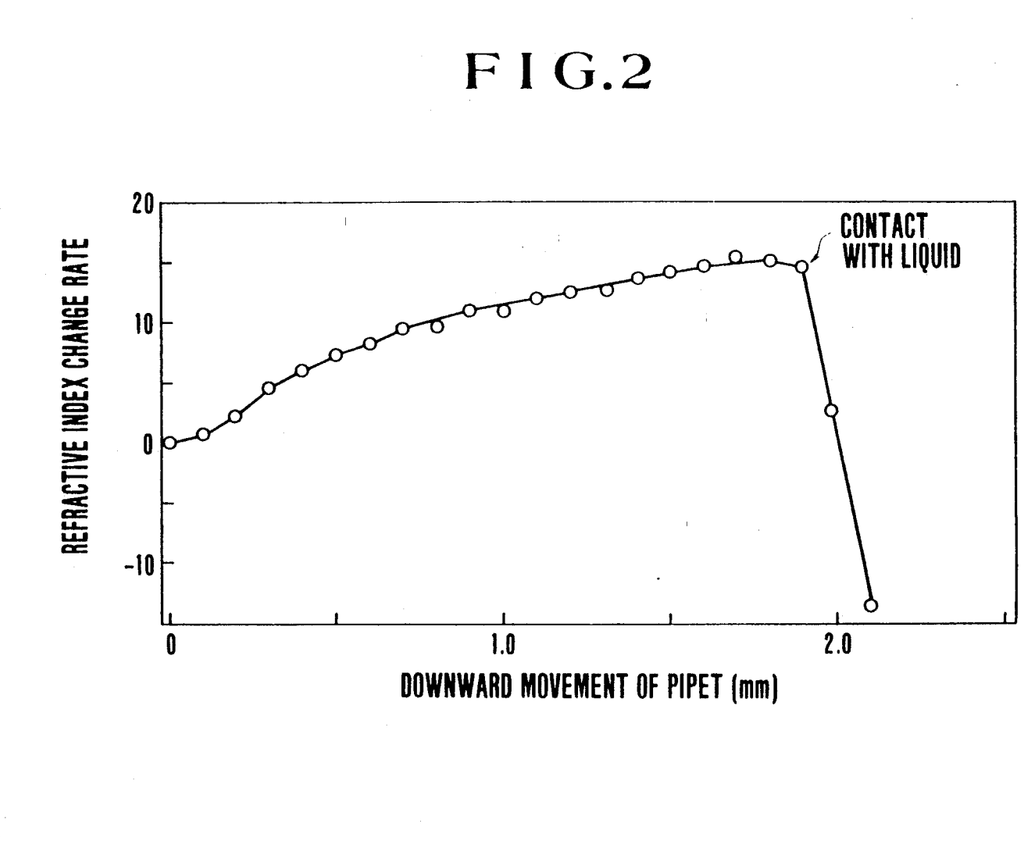
FIG. 2 illustrates the changes in intensity of the detected reflected light.

FIG. 2 illustrates the plots of the measurement results of the intensity of the reflected light detected by the detection circuit 8 as a function of time with a pipet instrument having a pipet tip moving downward as mentioned above. This drawing shows clearly that the intensity of the reflected light abruptly falls at the time of contact with the liquid surface.

FIGS. 3(a) to 3(d) schematically illustrate the change of reflection at the lower end of the pipet tip 3.

Figure 3A:
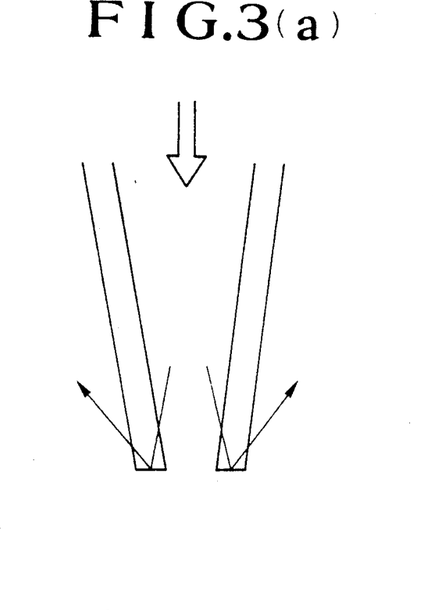
FIGS. 3(a) to 3(d) explain the change of reflected light at the tip end face of the pipet tip.

FIG. 3(a) shows that a part of the light projected to the inside of the pipet tip is reflected at the lower end thereof and the rest of the light passes through the tip cavity. The intensity of the portion of the light reflected at the lower end face of the tip is detected by the detection circuit 8.

Figure 3B:
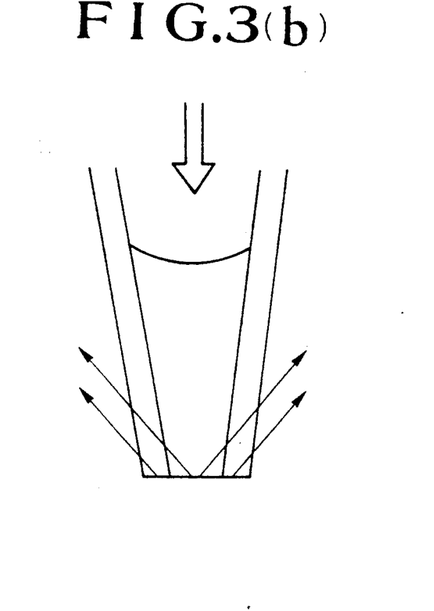

FIG. 3(b) schematically shows the reflection at the lower end of the pipet tip 3 which is holding a solution (in such a case where a dilution liquid is sucked in prior to sucking a liquid sample). The light having passed through the solution is reflected also at the end face of the solution, so that the intensity of the reflected light is larger than that shown in FIG. 3(a), especially when the light is less absorbed or less scattered by the solution.

Figure 3C:
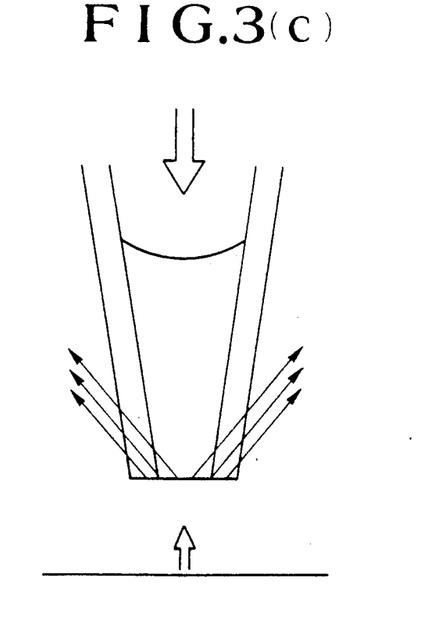

FIG. 3(c) schematically shows the intensity of the reflected light at the time when the pipet tip 3 shown in FIG. 3(b) is brought close to the liquid surface. The light reflected at the liquid surface gives influence in addition to the reflected light at the tip lower end and the face of the solution held in the tip, increasing further the intensity of the reflected light.

Figure 3D:
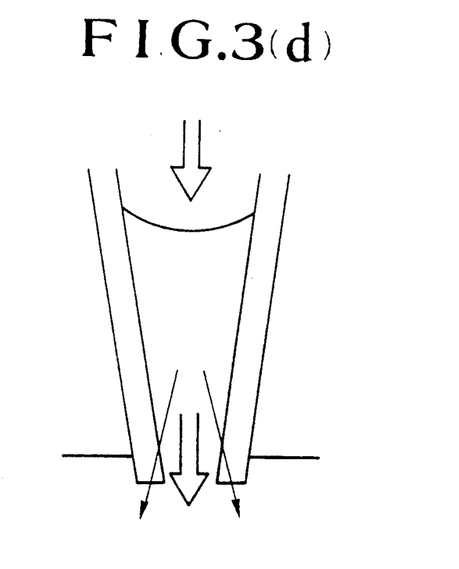

FIG. 3(d) schematically shows the reflection of light at the time when the pipet tip 3 is brought into contact with a liquid sample. In this state, the reflected light has become remarkably decreased since the difference of refractive indexes between the pipet tip and the surrounding external medium becomes less by the contact with the liquid.

The instrument of this example (the situation is the same in other examples) gives an advantageous effect in that the position of the lower end of the pipet tip in the liquid sample is precisely decided at the start of the liquid suction, and enables accurate quantitative sampling of a liquid. The instrument of this example gives an additional effect that the excess or insufficiency of the amount of the taken-out liquid can be confirmed by confirming the starting time and the finishing time of the liquid suction.

Figure 4A:
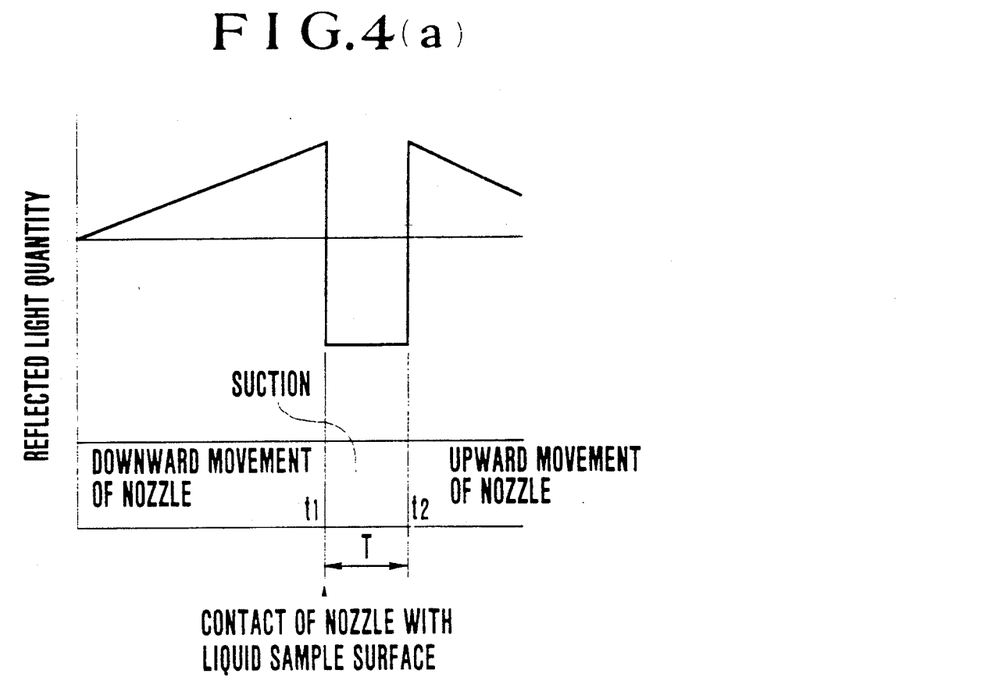
FIG. 4(a) and FIG. 4(b) schematically illustrate the changes in reflected light intensities in the cases where the liquid sampling is conducted quantitatively and accurately, and is conducted less quantitatively and less accurately.
Figure 4B:
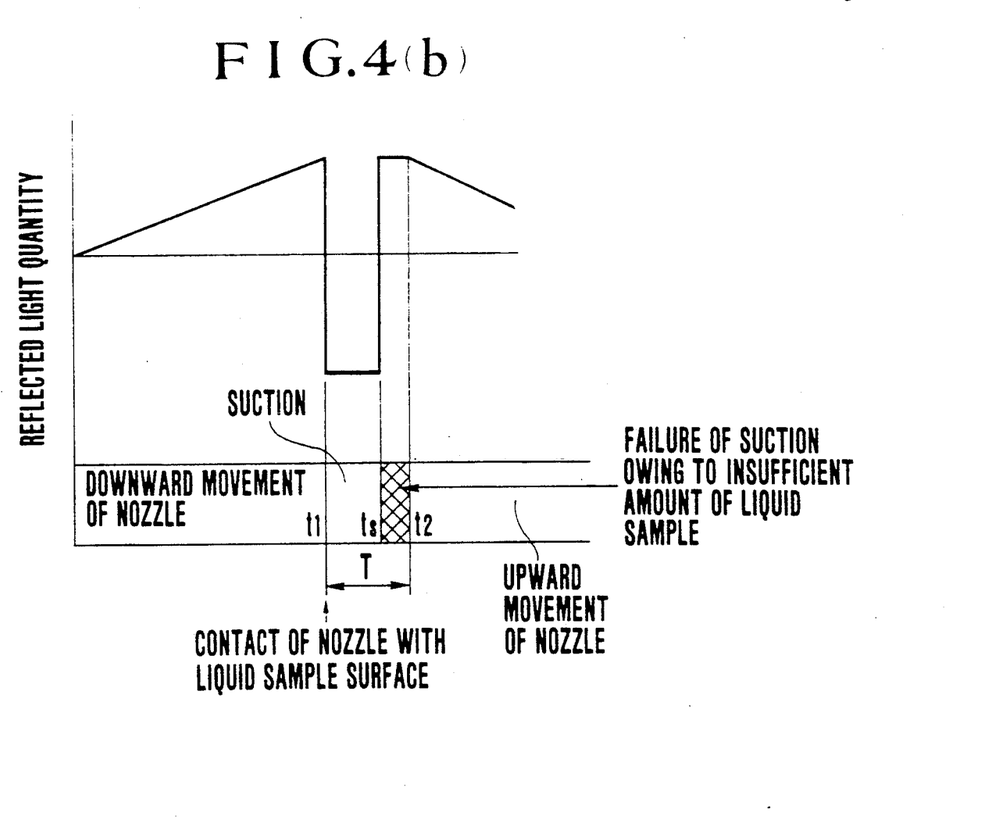

This is explained by reference to FIG. 4. In FIG. 4, the abscissa shows the lapse of time, and the ordinate shows the detected intensity of reflected light. Both FIG. 4(a) and FIG. 4(b) illustrate real measurement results of certain samples. In FIG. 4(a), the reflected light intensity gradually increases as the pipet tip is moved down toward the liquid sample. At the time when the tip comes to touch the liquid sample (at the time $t_1$ in the drawings), the light to be reflected comes to penetrate into the liquid sample, resulting in rapid fall of the light detection intensity. Then liquid suction is conducted at a predetermined negative pressure for a predetermined time T. After the lapse of the time T (the time $t_2$ in the drawings), the suction is stopped, and the pipet is moved up to become apart from the liquid sample, resulting in the abrupt rise of the intensity of the detected reflected light up to the intensity level before the time $t_1$.

In FIG. 4(b), a case is shown where the pipet tip comes to be separated from the liquid sample by some reason during the suction (at the time $t_s$). This separation of the pipet tip from the liquid sample is readily confirmed by restoration of the intensity of the detected reflected light at the time $t_S$. In this case, the amount of the sucked liquid becomes insufficient in correspondence with the shortage of time in comparison with the predetermined time T (as shown by the shadowed portion in the drawing).

In such a manner, the time length of the contact with the liquid is controlled and confirmed by measuring the change pattern of detected reflected light in applying negative pressure to the inside of the pipet tip contacting with the liquid sample, whereby sufficiency or insufficiency of the sucked amount of the liquid sample to be measured is confirmed in comparison with the predetermined sucked amount. Thus the instrument of the present invention gives excellent effect that an influence of a sampling error can be avoided practically which affects, for example, the result of diagnosis by an immune reaction measurement using liquid sample taken with this instrument, since the operation is conducted with confirmation of quantitative sampling of each liquid sample.

EXAMPLE 2

Figure 5:
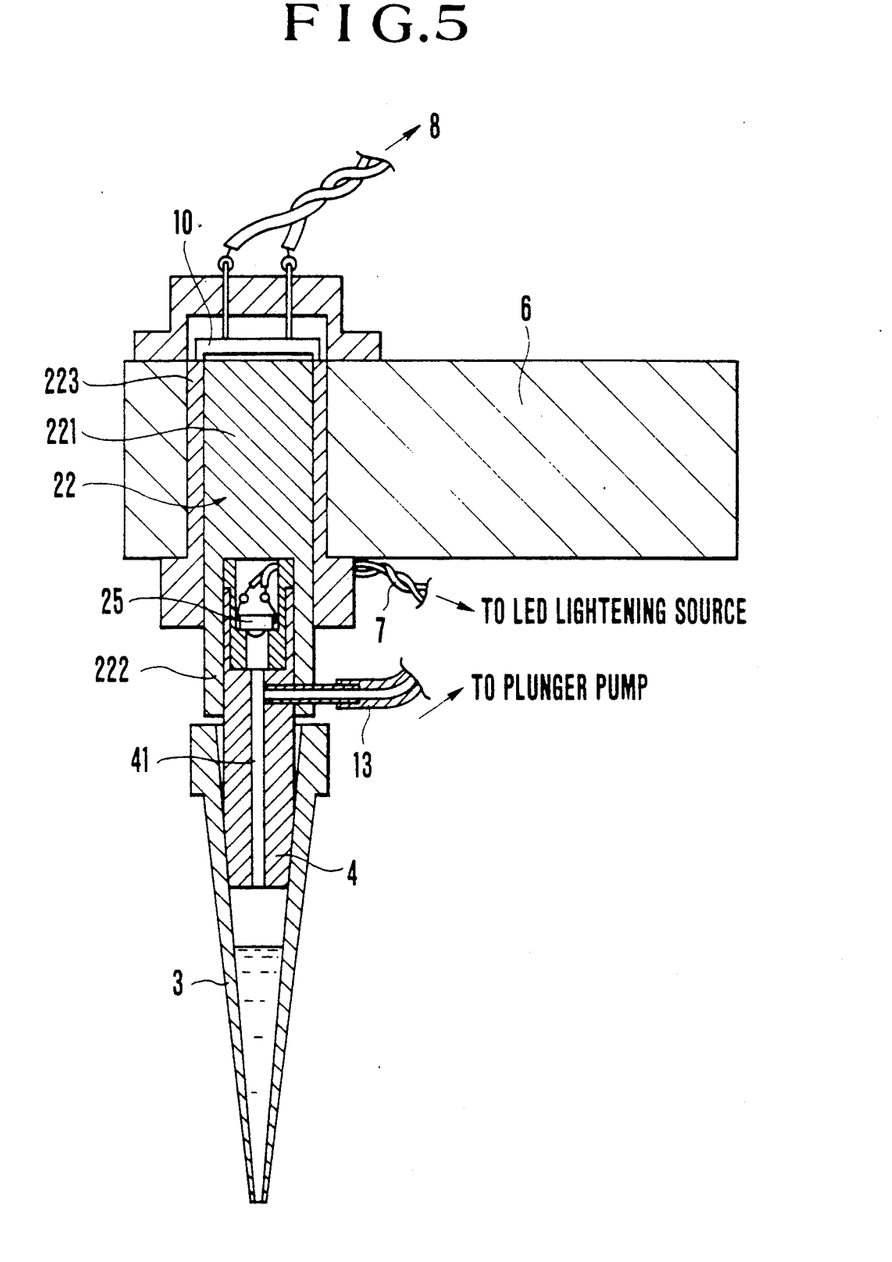
FIG. 5 schematically illustrates the constitution of the quantitative liquid sampling instrument of Example 2.

FIG. 5 illustrates the instrument of this example, which has a further characteristic with respect to the light-receiving means of the liquid level detecting device in comparison with Example 1.

The instrument of Example 2 is basically the same as that of Example 1 in that the main body of the pipet instrument is made up of a frame 6, and a pipet tip fitting tube portion 4, and a disposable type of pipet tip 3 is fitted detachably to the pipet tip fitting tube portion 4. However, the instrument of this example is different in that the pipet fitting tube portion 4 is fixed to the frame 6 through the light transmitting body 22.

The light transmitting body 22 in this example has a columnar portion 221 as the upper portion which is fixed to the frame 6, and an annular portion 222 which extends downward from the lower end periphery of the columnar portion 221. The pipet tip fitting tube portion 4 and a light-emitting element (LED) constituting a light-projection means are fixed in the inside of the annular portion 222. The lower end face of the annular potion 222 is opposed to the upper end face of the pipet tip 3 fitted to the pipet tip fitting tube portion 4. A cover 223 is provided to cover the light transmitting body 22. The pipet tip fitting tube 4 has a through-hole 41.

A photodiode 10 which is a light-receiving element of the light receiving means is fixed on the top of the frame 6 so as to confront the upper end face of the columnar portion 221 of the light-transmitting body 22. It is preferable that the photodiode 10 contacts face-to-face with its surface. Other constitutions are nearly the same as in Example 1, so that the designations of necessary portions only are shown here, other designations being omitted.

In the pipet instrument having the arrangement described above, the light reflected by the lower end face of the pipet tip is transmitted through the inside of the pipet tip to the upper end thereof, introduced to the annular portion 222 of the light transmitting body 22, and then transmitted through the columnar portion 221 of the light-transmitting body to the photodiode 10. With such an arrangement, the light reflected by the entire bottom end face of the pipet tip is to be received by the photodiode 10 through the above-mentioned path, whereby the utilization rate of the reflected light is greatly increased in comparison with the case where only a portion of the light reflected at the annular portion is detected (for example, the case where the photodiode is directly opposed to a limited portion of the annular upper end portion of the pipet tip).

Accordingly, a more clear detection of the abrupt change of the intensity of the reflected light is made feasible, or intensity of the light of the light source may be decreased for obtaining the same level of detection accuracy, advantageously.

The quantitative liquid sampling instrument of the present invention provides for the following advantages by solving various problems which are present in conventional instruments.

The instrument enables the accurate detection of the liquid surface level of a sample or the like in a container, realizing high accuracy in quantitative liquid sampling, which makes it possible to provide a quantitative liquid sampling instrument of high accuracy suitable, for example, for an immune diagnosis apparatus.

The instrument enables liquid level detection and liquid sucking simultaneously in one step with a micro quantity of sample as a measurement object, realizing rapid operation, which makes it feasible to constitute a quantitative liquid sampling instrument of automated or mechanized immune diagnosis apparatuses.

The instrument can prevent contamination between samples by use of a disposable type of pipet tip.

In the preferable constitution of the present invention, utilizing the tube shell of the pipet tip, the arrangement of the constituting members can be designed with high freedom, since a mechanical member for liquid level detection need not be placed around the pipet tip of the pipet instrument and interference of the pipet tip with other circumferential devices and members. In another preferable arrangement utilizing a light-transmitting body of the type of collecting light transmitted to the upper end face through the columnar portion, almost all of the reflected light is utilized for detection, giving high detection sensitivity and enabling a decrease of intensity of the light source.

In an embodiment utilizing, for detection, light of a nonvisible wavelength region such as light of infrared light region, the detection is not affected by external disturbance like room illumination, realizing a high accuracy of detection.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A quantitative liquid sampling instrument comprising:
   (a) a main body of a pipet device comprising: a pipet tip having a means defining an opening at a lower end of the pipet tip for sucking and discharging a liquid, said pipet tip being in a shape of a tube shell and having a cavity for holding a liquid sucked therein through the opening, said pipet tip being made of a transparent or semi-transparent material;
   (b) means for applying a gas pressure for sucking or discharging the liquid to or from an inside of the cavity of the pipet tip;
   (c) liquid level detecting means mounted on a frame of the main body of the pipet device, said liquid level detecting means comprising light projecting means for projecting light to the lower end of the pipet tip and light receiving means for receiving the light reflected by the lower end of the pipet tip, and employing an intensity of the received light as a detection information;

(d) vertical movement control means for moving the main body of the pipet device or a container of the liquid so as to make the main body of the pipet device and the container relatively approach one another until a length of a lower end of the pipet tip is dipped into the liquid in the container; and (e) computing means for computing an end point of relative approaching movement of the main body of the pipet device and the container and for outputting a signal regarding the end point to the vertical movement control means, wherein the computing means for computing the end point of the relative approaching movement of the main body of the pipet device and the container comprises means for detecting a substantially decrease int he intensity of the reflected light received by the light receiving means on contact of the pipet tip with the liquid and stopping the relative approaching movement of the main body of the pipet device and the container.

2. The quantitative liquid sampling instrument according to claim 1, wherein said pipet tip is detachably attached to said main body of the pipet device.

3. The quantitative liquid sampling instrument according to claim 1 or 2, wherein the pipet tip is in a shape approximately of an inverted truncated cone.

4. The quantitative liquid sampling instrument according to claim 3, wherein the lower end of the pipet tip is a horizontal face.

5. The quantitative liquid sampling instrument according to claim 4, wherein the vertical movement control means for moving the main body of the pipet device or a container of the liquid to relatively approach one another comprises means for driving the main body of the pipet device vertically.

6. The quantitative liquid sampling instrument according to claim 1, wherein the light projecting means is installed inside of the pipet tip, and the light receiving means is installed outside of the pipet tip.

7. The quantitative liquid sampling instrument according to claim 1, wherein the light projecting means is installed inside of the pipet tip, and the light receiving means is opposed to an upper end face of the tube-shell-shaped pipet tip.

8. The quantitative liquid sampling instrument according to claim 1, wherein the light projecting means is installed inside or outside of the pipet tip, and the light receiving means comprises a light transmitting body comprising an annular portion opposed to an annular upper end face of the tube-shell-shaped pipet tip and a columnar portion provided continuously on the annular portion, and a light receiving sensor opposed to an upper end face of the columnar portion.

9. The quantitative liquid sampling instrument according to claim 8, wherein a wavelength of the light projected from the light projecting means is within the range of from 200 nm to 1100 nm.

* * * * *